(12) United States Patent
Chak et al.

(10) Patent No.: US 12,262,879 B2
(45) Date of Patent: Apr. 1, 2025

(54) DEVICE FOR BIOLOGICAL CELL COLLECTION AND METHOD OF USE

(71) Applicant: Case Western Reserve University, Cleveland, OH (US)

(72) Inventors: Amitabh Chak, Cleveland, OH (US); Sanford Markowitz, Cleveland, OH (US); Dennis Siedlak, Cleveland, OH (US); Joseph Willis, Cleveland, OH (US); Lishan Aklog, Purchase, NY (US); Michael Boutillette, San Francisco, CA (US); Richard Yazbeck, Norwell, MA (US)

(73) Assignee: Case Western Reserve University, Cleveland, OH (US)

( * ) Notice: Subject to any disclaimer, the term of this patent is extended or adjusted under 35 U.S.C. 154(b) by 213 days.

(21) Appl. No.: 16/902,579

(22) Filed: Jun. 16, 2020

(65) Prior Publication Data

US 2021/0386410 A1    Dec. 16, 2021

(51) Int. Cl.
*A61B 10/02*      (2006.01)
*A61B 10/04*      (2006.01)
*A61M 25/10*      (2013.01)

(52) U.S. Cl.
CPC .......... *A61B 10/0283* (2013.01); *A61B 10/04* (2013.01); *A61M 25/10182* (2013.11); *A61M 25/1025* (2013.01); *A61M 25/1038* (2013.01); *A61B 2010/0216* (2013.01); *A61M 2025/1086* (2013.01); *A61M 2025/1088* (2013.01)

(58) Field of Classification Search
CPC .............. A61B 10/0283; A61B 10/04; A61B 2010/0216; A61M 25/10182; A61M 25/1025; A61M 25/1038; A61M 2025/1086; A61M 2025/1088
See application file for complete search history.

(56) References Cited

U.S. PATENT DOCUMENTS

| 1,098,222 A | 5/1914 | Brasefield |
| 3,400,708 A | 9/1968 | Scheidt |

(Continued)

FOREIGN PATENT DOCUMENTS

| CN | 202104944 U | 1/2012 |
| CN | 105193459 A | 12/2015 |

(Continued)

OTHER PUBLICATIONS

International Search Report in International Application No. PCT/US2018/030907 mailed Sep. 17, 2018.

(Continued)

*Primary Examiner* — Rene T Towa
(74) *Attorney, Agent, or Firm* — Greenberg Traurig, LLP; Chinh H. Pham; Andrew Cull

(57) ABSTRACT

A device for collecting a biological sample in a subject, the device including an inflatable portion attached to a tubular member, and designed to expand from within the tubular member when inflated and to retract within the tubular member, a surface on the inflatable portion provided with varied thickness to facilitate movement of the inflatable portion between an expanded state and a retracted state, and a plurality of projections on the surface to allow collection of the biological sample when the inflatable portion is in the expanded state.

16 Claims, 12 Drawing Sheets

(56) References Cited

U.S. PATENT DOCUMENTS

| | | | |
|---|---|---|---|
| 3,664,328 A | 5/1972 | Moyle et al. | |
| 4,467,816 A | 8/1984 | Schluter et al. | |
| 4,481,952 A | 11/1984 | Pawelec | |
| 4,627,444 A | 12/1986 | Brooker | |
| 4,735,214 A | 4/1988 | Berman | |
| 4,979,951 A | 12/1990 | Simpson | |
| 5,318,587 A | 6/1994 | Davey | |
| 5,445,164 A | 8/1995 | Worthen et al. | |
| 5,879,499 A * | 3/1999 | Corvi | A61M 25/0012 604/524 |
| 7,004,913 B1 | 2/2006 | Rutenberg et al. | |
| 7,108,661 B2 | 9/2006 | Secrest et al. | |
| 7,485,420 B2 | 2/2009 | Markowitz | |
| 7,964,353 B2 | 6/2011 | Markowitz | |
| 8,068,897 B1 | 11/2011 | Gazdzinski | |
| 8,221,977 B2 | 7/2012 | Markowitz | |
| 8,415,100 B2 | 4/2013 | Markowitz et al. | |
| 8,481,707 B2 | 7/2013 | Markowitz et al. | |
| 8,642,271 B2 | 2/2014 | Markowitz et al. | |
| 8,668,654 B1 | 3/2014 | Gerrans et al. | |
| 9,339,259 B2 | 5/2016 | Loktionov et al. | |
| 9,580,754 B2 | 2/2017 | Markowitz et al. | |
| 10,660,621 B2 | 5/2020 | Markowitz et al. | |
| 2002/0173816 A1 | 11/2002 | Hung | |
| 2003/0004535 A1* | 1/2003 | Musbach | A61M 25/1029 604/103.08 |
| 2003/0040681 A1 | 2/2003 | Ng et al. | |
| 2003/0208134 A1 | 11/2003 | Secrest et al. | |
| 2004/0127932 A1 | 7/2004 | Shah | |
| 2005/0043649 A1* | 2/2005 | Urie | A61B 5/037 600/587 |
| 2005/0215959 A1 | 9/2005 | Whitington | |
| 2006/0184191 A1 | 8/2006 | O'Brien | |
| 2006/0189891 A1 | 8/2006 | Waxman et al. | |
| 2006/0271061 A1 | 11/2006 | Beyar et al. | |
| 2007/0239066 A1 | 10/2007 | Laham et al. | |
| 2008/0097238 A1 | 4/2008 | Loktionov et al. | |
| 2008/0188769 A1 | 8/2008 | Lu | |
| 2008/0243031 A1 | 10/2008 | Seibel | |
| 2009/0024060 A1 | 1/2009 | Darrigrand et al. | |
| 2009/0118641 A1 | 5/2009 | Van Dam et al. | |
| 2009/0299401 A1* | 12/2009 | Tilson | A61M 25/1029 606/192 |
| 2010/0280490 A1* | 11/2010 | Schertiger | A61M 25/1025 604/514 |
| 2010/0286593 A1 | 11/2010 | Krolik et al. | |
| 2012/0164638 A1 | 6/2012 | Vogelstein et al. | |
| 2013/0066346 A1 | 3/2013 | Pigott | |
| 2013/0116596 A1 | 5/2013 | Birnboim et al. | |
| 2013/0131329 A1 | 5/2013 | Markowitz et al. | |
| 2013/0267870 A1 | 10/2013 | Lonky et al. | |
| 2014/0113290 A1 | 4/2014 | Markowitz et al. | |
| 2014/0171828 A1 | 6/2014 | Blitzer et al. | |
| 2014/0214085 A1 | 7/2014 | Druma | |
| 2014/0296742 A1 | 10/2014 | Kalloo et al. | |
| 2014/0323908 A1 | 10/2014 | Fitzgerald et al. | |
| 2015/0057517 A1 | 2/2015 | Pease et al. | |
| 2015/0289752 A1 | 10/2015 | Rachlin et al. | |
| 2015/0351729 A1 | 12/2015 | Corporation | |
| 2015/0374436 A1* | 12/2015 | Subramaniam | A61B 18/1492 606/41 |
| 2016/0081671 A1 | 3/2016 | Lubinski et al. | |
| 2016/0317132 A1* | 11/2016 | Markowitz | A61B 10/02 |
| 2017/0112477 A1 | 4/2017 | Benning et al. | |
| 2018/0116645 A1 | 5/2018 | Nosler | |
| 2018/0146839 A1 | 5/2018 | Friedlander et al. | |
| 2018/0161020 A1 | 6/2018 | Friedlander | |
| 2019/0081671 A1 | 1/2019 | Peris | |
| 2019/0261962 A1 | 8/2019 | Markowitz et al. | |
| 2019/0365276 A1 | 12/2019 | Vaezi et al. | |
| 2020/0022685 A1 | 1/2020 | Brodbeck et al. | |
| 2020/0077992 A1 | 3/2020 | Markowitz et al. | |
| 2021/0315551 A1 | 10/2021 | Smadi et al. | |
| 2021/0369256 A1 | 12/2021 | Markowitz et al. | |
| 2021/0386410 A1 | 12/2021 | Chak et al. | |
| 2022/0096060 A1 | 3/2022 | Markowitz et al. | |
| 2022/0096061 A1 | 3/2022 | Markowitz et al. | |
| 2022/0096062 A1 | 3/2022 | Markowitz et al. | |
| 2022/0096063 A1 | 3/2022 | Markowitz et al. | |
| 2022/0096064 A1 | 3/2022 | Markowitz et al. | |
| 2023/0000474 A1 | 1/2023 | Markowitz et al. | |
| 2023/0000475 A1 | 1/2023 | Markowitz et al. | |

FOREIGN PATENT DOCUMENTS

| | | | | |
|---|---|---|---|---|
| GB | 1573819 A | | 8/1980 | |
| JP | 59064065 A | | 4/1984 | |
| JP | 60052817 A | | 3/1985 | |
| JP | 2005168910 A | | 6/2005 | |
| JP | 2007222387 A | | 9/2007 | |
| JP | 2008541851 A | | 11/2008 | |
| JP | 2010505592 A | | 2/2010 | |
| JP | 2015196040 A | | 11/2015 | |
| JP | 2016516491 A | | 6/2016 | |
| JP | 2017038884 A | | 2/2017 | |
| JP | 2017064067 A | | 4/2017 | |
| WO | 1987005523 A1 | | 9/1987 | |
| WO | 1989006360 A1 | | 7/1989 | |
| WO | 1994023787 A1 | | 10/1994 | |
| WO | WO-9423787 A1 | * | 10/1994 | ........ A61M 25/1002 |
| WO | 2000054829 A2 | | 9/2000 | |
| WO | WO-0054829 A2 | * | 9/2000 | ............ A61M 25/10 |
| WO | 2004110300 A2 | | 12/2004 | |
| WO | 2004110300 A3 | | 12/2004 | |
| WO | 2006003447 A1 | | 1/2006 | |
| WO | 2012162610 A1 | | 11/2012 | |
| WO | 2013040160 A1 | | 3/2013 | |
| WO | 2013116560 A1 | | 8/2013 | |
| WO | 2014121207 A1 | | 8/2014 | |
| WO | 2014143459 A1 | | 9/2014 | |
| WO | 2014170393 A1 | | 10/2014 | |
| WO | 2015089422 A1 | | 6/2015 | |
| WO | 2016034888 A1 | | 3/2016 | |
| WO | 2016178189 A1 | | 11/2016 | |
| WO | 2017147586 A1 | | 8/2017 | |
| WO | 2018204659 A1 | | 11/2018 | |

OTHER PUBLICATIONS

International Search Report in International Application No. PCT/US2020/037883 mailed Sep. 25, 2020.

Capsule Size Guide, LFA Machines Oxford LTD., https://www.lfacapsulefillers.com/capsule-size-chart.

Intubation, www.merriam-webster.com/dictionary/intubation, 11 pages, printed on Mar. 17, 2022.

Businello et al., "The Pathologic and Molecular Landscape of Esophageal Squamous Cell Carcinogenesis," Cancers, Aug. 4, 2020, vol. 12, No. 2160, pp. 1-20.

Clancy et al., "Diagnosing Invasive Candidiasis," Journal of Clinical Microbiology, May 2018, vol. 56, No. 5, pp. e01909-17.

Dioverti et al., "Cytomegalovirus," Microbiology Spectrum, Jul. 15, 2016, vol. 4, No. 4.

Esophagus, Britannica's public website, www.britannica.com/science/human-digestive-system/Esophagus, 16 pages, printed on Jun. 27, 2022 (Year: 2022).

Srinagesh et al., "Biomarkers in Acute Graft-versus-Host Disease: New Insights," Therapeutic Advances in Hematology, 2019, vol. 10, pp. 1-8.

Richard Demay et al., "The Art and Science of Cytopathology," (1996) First Edition (TEXTBOOK).

Goldblum and Odze, "Surgical Pathology of the GI Tract, Liver, Biliary Tract and Pancreas," (2015) Third Edition (TEXTBOOK).

"Motility Diagnostic Services | UC Davis Health", Health.ucdavis.edu/internalmedicine/gastro/esophmanometry.html, 2 pages, printed on Apr. 25, 2023. (Year: 2023).

* cited by examiner

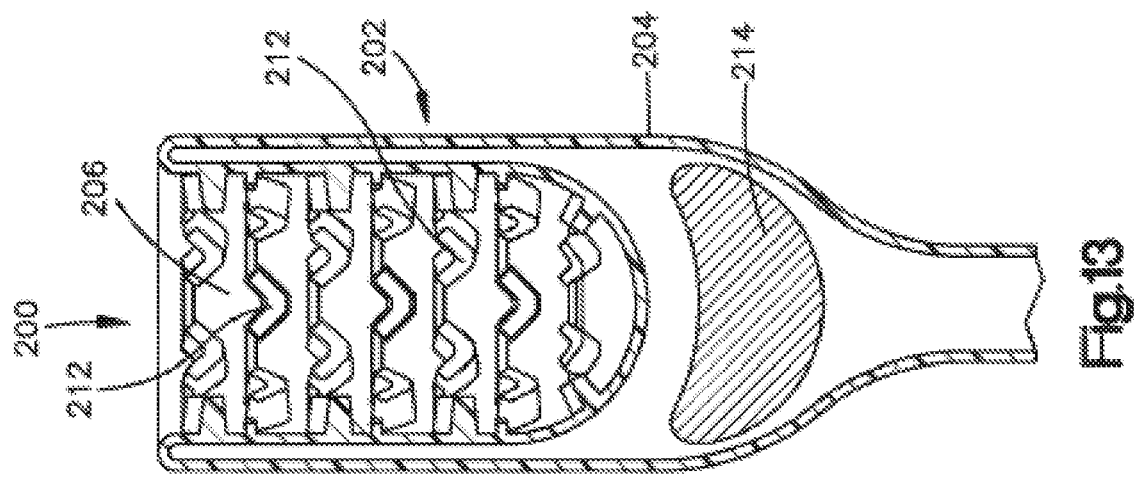
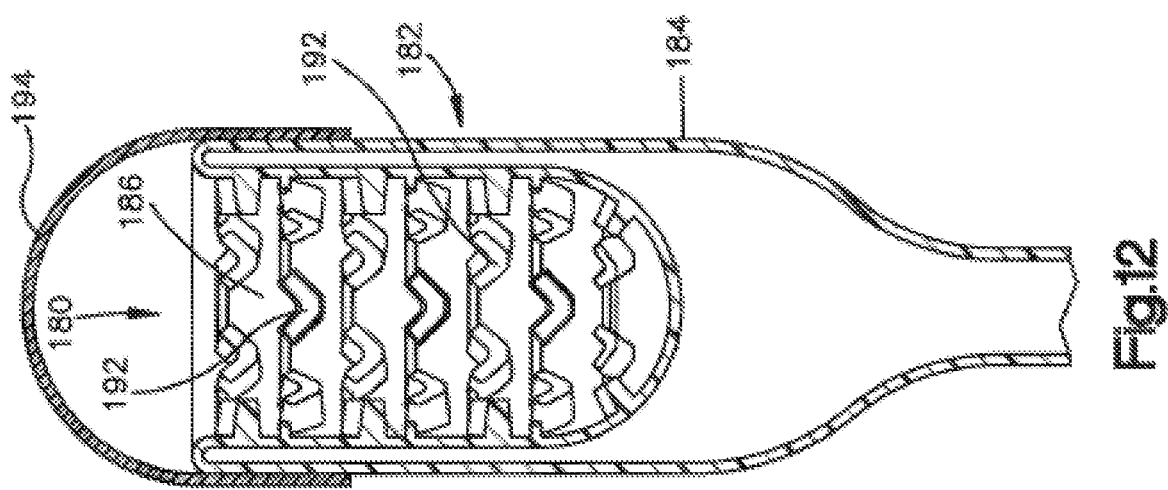

DEVICE FOR BIOLOGICAL CELL COLLECTION AND METHOD OF USE

GOVERNMENT FUNDING

This invention was made with government support under Grant Nos. P50CA150964, U01CA152756, U54CA163060 awarded by The National Institutes of Health. The United States government has certain rights to the invention.

FIELD OF THE INVENTION

The present disclosure relates to systems and methods suitable for collecting biological samples. In particular, the present disclosure relates to a biological sample collection device that includes an expandable device that can be designed for collecting samples and retracting into a proximal end portion.

BACKGROUND

Generally, a known tissue collection device includes an expandable device with longitudinally extending folds. The expandable device expands radially at a collection site within a body lumen, such as an esophagus. After the device is expanded, tissue is collected from the collection site. The expandable device is deflated after tissue is collected. The folds trap collected tissue when the device is deflated after collection of the tissue. The known tissue collection device may be inserted through an endoscope to the collection site or via standard catheter intubation techniques.

SUMMARY

There is a need for improvements for collecting biological samples. The present disclosure provides, in various embodiments solutions to address this need, in addition to having other desirable characteristics. The present disclosure is directed to a device for collecting a biological sample, and more specifically, to a device for collecting a biological sample, such as tissue, cells, protein, RNA and/or DNA from an esophagus of a subject.

In accordance with example embodiments of the present invention, a device for collecting a biological sample in a subject is provided. The device includes an inflatable portion attached to a tubular member, and designed to expand from within the tubular member when inflated and to retract within the tubular member, a surface on the inflatable portion provided with varied thickness to facilitate movement of the inflatable portion between an expanded state and a retracted state, and a plurality of projections on the surface to allow collection of the biological sample when the inflatable portion is in the expanded state.

In accordance with aspects of the present invention, the varied thickness is defined by a thinner distal end of the inflatable portion relative to a proximal end of the inflatable portion. The varied thickness can be defined by collapsible folds circumferentially situated about the surface of the inflatable portion. The inflatable portion can include a plurality of different durometer levels to facilitate a combination of inflation, expansion, deflation, and retraction. The inflatable portion can be removable from and replaceable on the tubular member using at least one of a friction fit or a mechanical fit. The varied thickness can be defined by ridges circumferentially positioned about the surface of the inflatable portion. The plurality ridges can be positioned between each row of the plurality of projections to vary inflation size and shape of the inflatable portion. The plurality ridges can help collect the biological sample. The inflatable portion can include drafting extending along the length of each row of the plurality of projections to create a variable stiffness of the inflatable portion. The tubular member can be a catheter coupled to the inflatable portion at a proximal and a connector at a distal end.

In accordance with aspects of the present invention, the connector can be a Y-fitting with a first branch extending at an angle to a second branch of the connector, the second including a stopcock. The inflatable portion can have an outer surface facing radially outwardly when the inflatable portion is in the expanded condition, the outer surface facing radially inwardly when the inflatable portion is in the retracted position. A first side wall of a tissue collecting projection can extend generally perpendicular to the outer surface of the inflatable portion and a second wall of the tissue collection projection tapers toward the first side wall as the side walls extend radially outward from the outer surface when the inflatable portion is in a non-inflated position between the retracted and expanded positions. At least one of the plurality of projections can have a V-shape, the first side wall facing in a proximal direction and forming an inner wall of the V-shape, the second side wall facing in a distal direction and forming an outer wall of the V-shape. The inflatable portion has a durometer between 20-70 Shore A. The device can further include a cap extending over the inflatable portion when the inflatable portion is in the retracted position to retain the inflatable portion in the retracted position. The expanded state can be facilitated by presence of positive pressure. The retracted state can be facilitated by presence of negative pressure.

BRIEF DESCRIPTION OF THE FIGURES

These and other characteristics of the present disclosure will be more fully understood by reference to the following detailed description in conjunction with the attached drawings, in which:

FIG. 12 is a schematic sectional view of a collection device constructed in accordance with a fourth embodiment of the present disclosure;

FIG. 13 is a schematic sectional view of a collection device constructed in accordance with fifth embodiment of the present disclosure;

DETAILED DESCRIPTION

Figure 3:
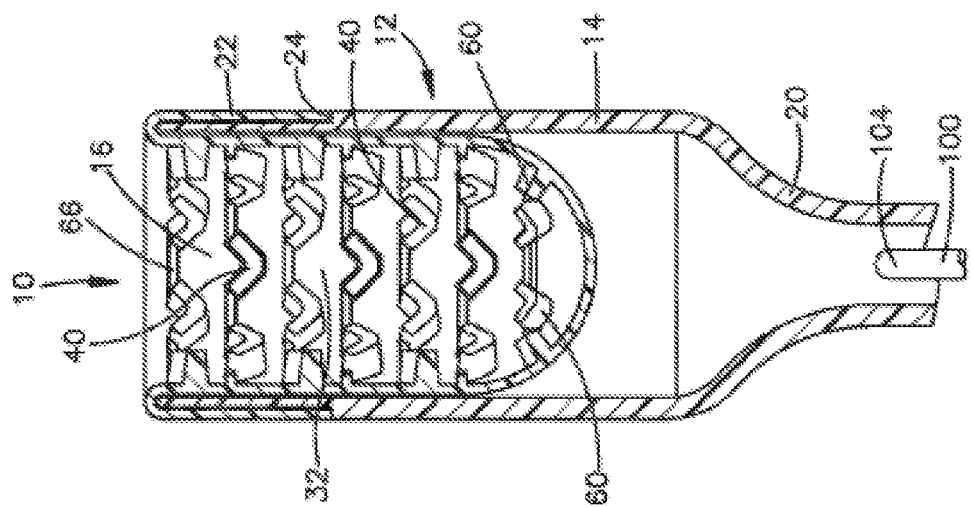
FIG. 3 is a sectional view of the collection device of FIG. 2.

In some embodiments, the device of the present disclosure can be used for collecting a biological sample in a subject. The device can include an inflatable distal end portion attached to a tubular support member. The inflatable distal end portion can be designed to expand from within a proximal end portion that is coupled to or part of the tubular support member. The inflatable distal end portion can be inflated outward from proximal end portion, expanded outside the proximal end portion, and retracted within the proximal end portion when deflated. In some embodiments, a surface on the inflatable distal end portion can be provided with varied levels of thickness to facilitate movement of the inflatable distal end portion between an expanded state and a retracted state. The varied thickness of the inflatable distal end portion can be provided to assist in any combination of inflation, expansion, deflation, and retraction of the inflatable distal end portion in relation to the proximal end portion. The varied thickness can also influence the shape and flexibility/rigidity of the inflatable distal end portion when in any of the any combination of inflation, expansion, deflation, and retraction of the inflatable states. In some embodiments, the surface of the inflatable distal end portion can include a plurality of projections or bristles positioned on the surface to allow collection of a biological sample when the inflatable distal end portion is in the expanded state. The projections or bristles positioned on the surface can also be accompanied by formations (e.g., ridges, valleys, etc.) formed by the varied thickness of the inflatable distal end portion.

FIGS. 1 through 18, wherein like parts are designated by like reference numerals throughout, illustrate an example embodiment or embodiments of improved operation for biological sample collection, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

A collection device 10 for collecting a biological sample constructed in accordance with the present disclosure is illustrated in FIGS. 1-9. The collection device 10 may be used to collect tissue, cells, protein, RNA and/or DNA from a body lumen, such as an esophagus of a subject. As discussed herein, the use of the term subject can refer to a human patient, an animal subject or any other combination of objects that may have a section that requires sampling. The tissue, cells, protein, RNA and/or DNA collected from the esophagus may be used in any one of the methods disclosed in U.S. patent application Ser. No. 14/109,041, U.S. patent application Ser. No. 13/670,155, U.S. patent application Ser. No. 13/263,020, U.S. Pat. Nos. 8,642,271, 8,481,707, 8,415,100, 8,221,977, 7,964,353, 7,485,420, and 10,660,621 which are incorporated herein by reference in their entirety.

The collection device 10 includes a generally hollow longitudinally extending collection portion 12. The collection portion 12 has a first or proximal axial end portion 14 connected to a second or distal axial end portion 16. The distal end portion 16 has a first axial end portion 22 connected to the proximal axial end portion 14. The first end portion 22 may be connected to the proximal end portion 14 in any desired manner, such as by using an adhesive or bonding. The first axial end portion 22 engages a shoulder 24 on the proximal axial end portion 14. Therefore, the collection portion 12 has a smooth outer surface. The distal axial end portion 16 may be connected to the proximal end portion 14 in any desired manner. The proximal axial end portion 14 and the distal axial end portion 16 may be made of a flexible polymer, such as silicone or polyurethane. The distal axial end portion 16 has a lower durometer than the proximal axial end portion 14. The distal axial end portion 16 may have a durometer between 5-90 Shore A. The durometer of the distal axial end portion 16 is preferably between 20-70 Shore A, and more specifically, approximately 30 Shore A.

The distal axial end portion 16 may expand and contract. The first or proximal axial end portion 14 is relatively rigid. Therefore, the proximal end portion 14 has a fixed radial extent. The first axial end portion 14 and the second axial end portion 16 may be formed as separate pieces that are connected together in any desire manner or may be integrally formed as one-piece. Although the proximal end portion 14 is illustrated as having a cylindrical shape, the proximal end portion may have any desired shape.

The proximal axial end portion 14 is connected to a support member 20, such as a catheter. The support member 20 may be a tubular member in fluid communication with the interior of the collection portion 12. The proximal axial end portion 14 conducts fluid, such as air, from the support member 20 to the distal axial end portion 16. The support 20 resists collapsing when a vacuum is applied to the support member and resists stretching during withdrawal of the collection device 10 from the collection site.

Figure 2:
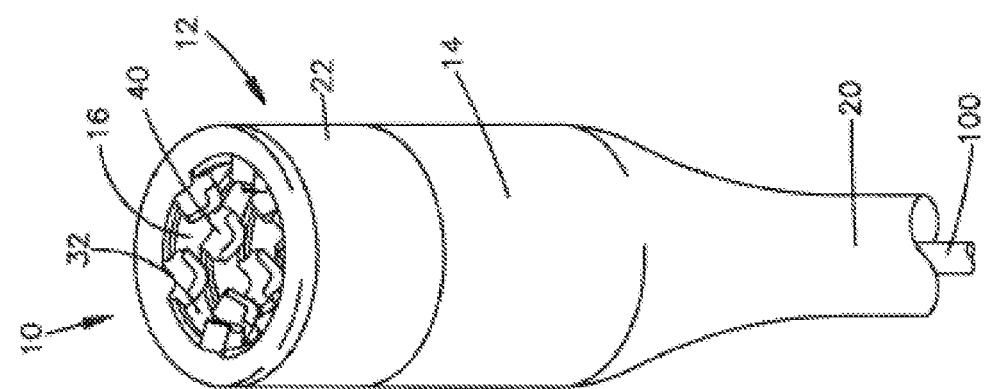
FIG. 2 is a schematic pictorial view of the collection device of FIG. 1 shown in a collapsed position.

The second or distal end portion 16 of the collection portion 12 has an expanded or inflated position (FIG. 1) and a collapsed or deflated position (FIGS. 2-3). The expanded position shown in FIG. 1 may be one of many expanded positions for the distal end portion 16. It is contemplated that the distal end portion 16 may expand more than shown in FIG. 1 so that the distal end portion obtains a more spherical shape and looks similar to a hot air balloon. The distal end portion 16 has a convex shape, shown in FIG. 1, when in the expanded or inflated position. The distal end portion 16 may extend radially outward a greater distance than the proximal end portion 14 when in the expanded position.

The distal end portion 16 extends into the first or proximal axial end portion 14 and has a concave shape, shown in FIGS. 2 and 3, when in the collapsed or deflated position. The distal end portion 16 may be retracted when in the collapsed position. The distal end portion 16 extends axially into the interior of the proximal end portion 14 when in the collapsed or deflated position. Therefore, the distal end portion 16 moves axially or longitudinally relative to the proximal end portion 14 when moving between the deflated and inflated positions. The relatively lower durometer of the distal end portion 16 allows the distal end portion to extend axially into the interior of the proximal end portion 14 and have a concave shape when in the collapsed position. The distal end portion 16 may be biased into the collapsed or deflated position in any desired manner.

The proximal end portion 14 has a relatively high durometer so that the proximal end portion does not collapse when a vacuum is applied to the proximal end portion through the support 20. The shape of the proximal end portion 14 does not change when the distal end portion 16 moves between the deflated and inflated positions. The proximal end portion 14 does not move radially when the distal end portion 16 moves between the deflated and inflated positions.

The distal end portion 16 has an outer surface 32 for collecting tissue when the distal portion is in the expanded position. The outer surface 32 faces radially outwardly when the distal end portion 16 is in the expanded position and may face radially inwardly when the distal end portion is in the collapsed or retracted position. It is contemplated that the outer surface 32 of the distal end portion 16 may have any desired construction for collecting tissue. The outer surface 32 of the distal end portion 16 may have a plurality of projections or bristles 40 for collecting tissue. The distal end portion 16 may have any desired number of projections or bristles 40.

Figure 1:
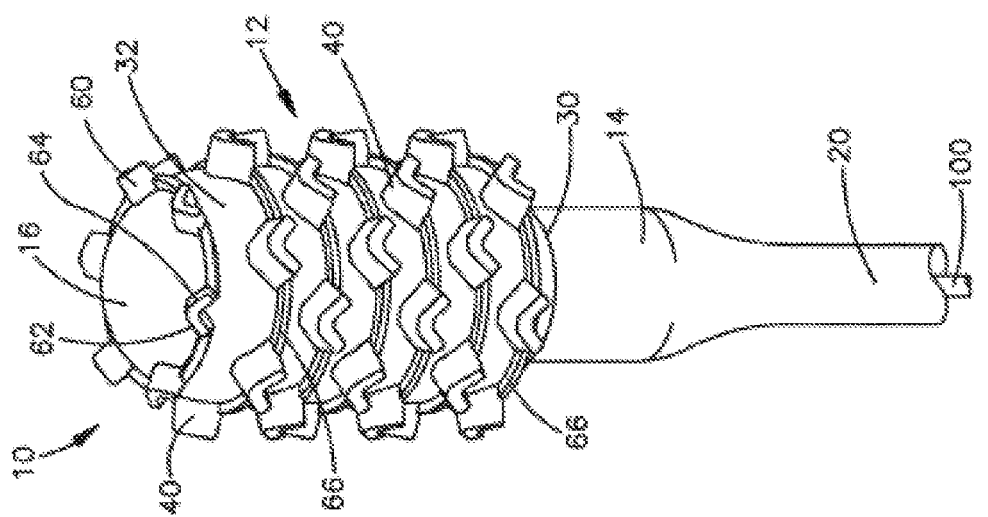
FIG. 1 is a schematic pictorial view of a biological sample collection device constructed in accordance with the present disclosure.
Figure 4:
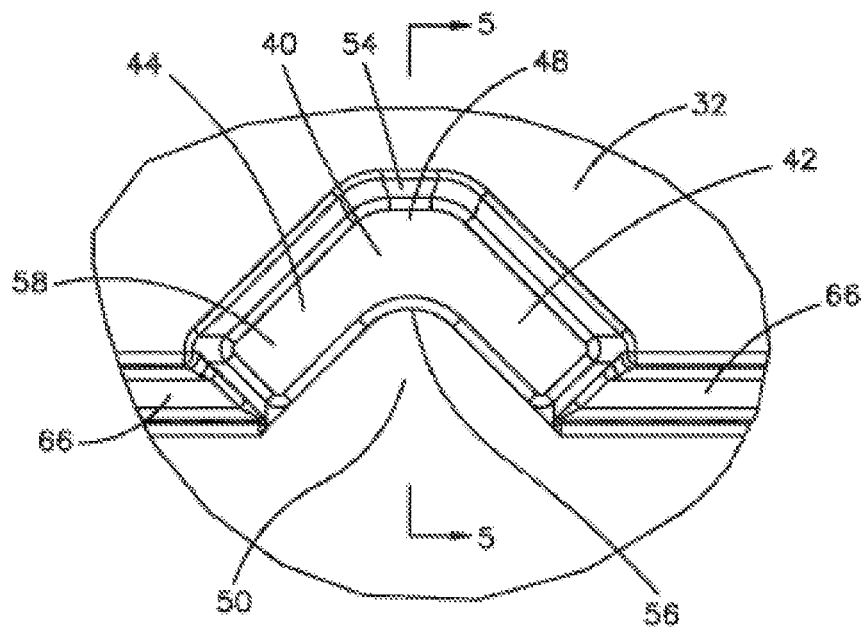
FIG. 4 is an enlarged plan view of a projection or bristle of the collection device of FIG. 1.
Figure 5:
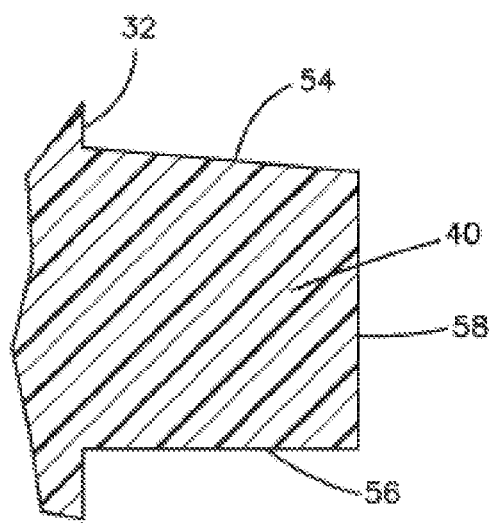
FIG. 5 is a sectional view of the projection taken along the line 5-5 in FIG. 4.
Figure 6:
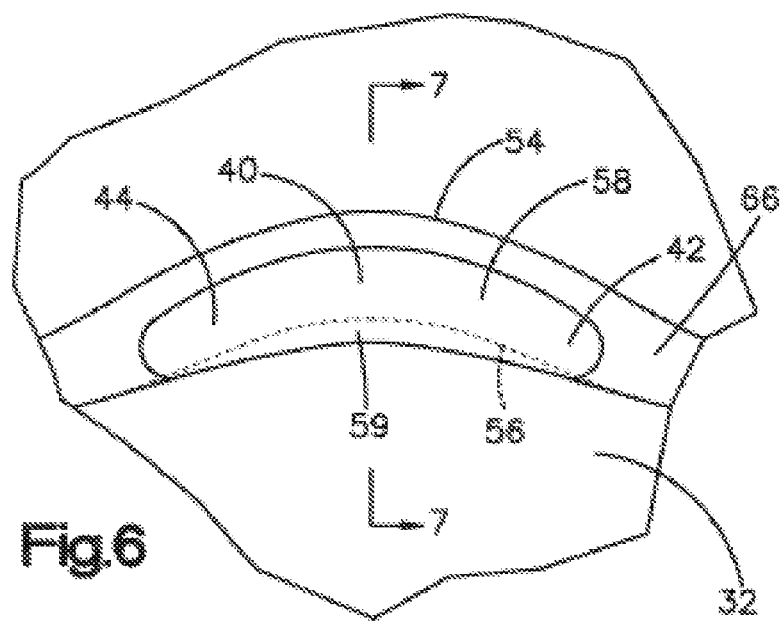
FIG. 6 is an enlarged plan view of the projection shown after expansion of a portion of the collection device.
Figure 7:
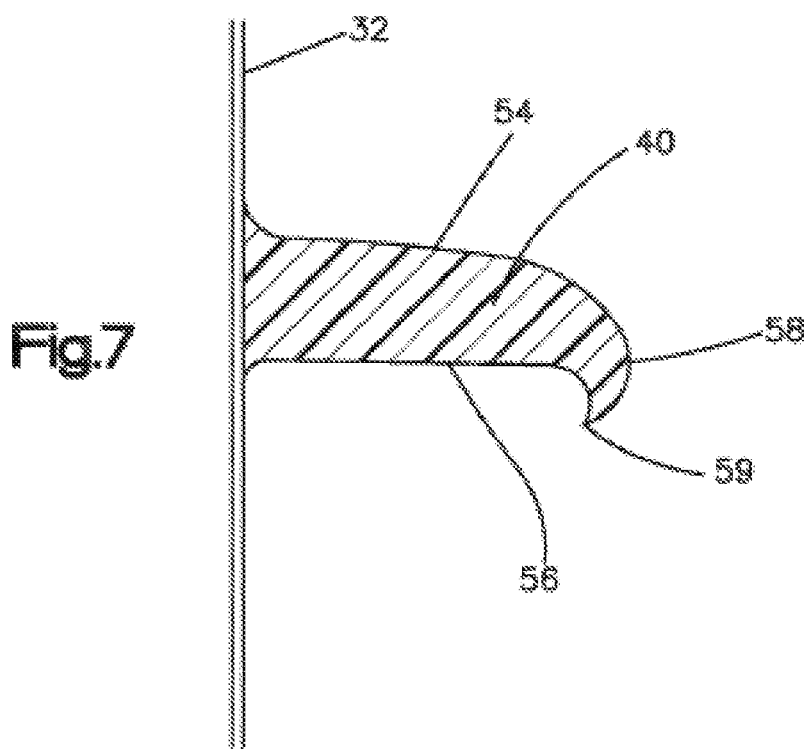
FIG. 7 is a schematic view of the projection after expansion of the portion of the collection device taken along the line 7-7 in FIG. 6.

The projections or bristles 40 may have a V-shape (FIG. 4). Each projection 40 has a first side 42 and a second side 44 extending from an intersection 48. The first and second sides 42, 44 extend in a generally proximal direction from the intersection 48 when the distal end portion 16 is in the expanded position (FIG. 1). The first and second sides 42, 44 extend in a generally distal direction when the distal end portion 16 is in the collapsed or retracted position (FIGS. 2 and 3). The first and second sides 42, 44 define a cup 50 for receiving collected biological samples. The cup 50 faces in a proximal direction when the distal portion 16 is in the expanded position and faces in a distal direction when the distal portion is in the collapsed position.

The first and second sides 42, 44 may extend at an angle of approximately 90° relative to each other. It is contemplated that the first and second sides 42 and 44 may extend at any desired angle relative to each other. The desired angle may be determined based on the type of biological sample to be collected. Alternatively, the projections 40 may be cup shaped or have a semi-circular shape.

Each of the projections or bristles 40 has side walls 54 and 56 (FIG. 5) that extend radially outward from the outer surface 32 when the distal portion 16 is in the expanded position. The side wall 56 faces the proximal direction when the distal portion is in the expanded position and forms an inner side of the cup 50. The side wall 54 faces the distal direction when the distal portion is in the expanded position and forms an outer wall of the cup 50. The side walls 54 and 56 extend from the outer surface 32 to a radially outer surface 58 of the projection 40. The side wall 56 extends generally perpendicular to the outer surface 32 and the outer surface 58 of the projection 40 when the distal end portion 16 is in a non-inflated position between the expanded and collapsed positions. The side wall 54 tapers toward the side wall 56 as the side wall 54 extends from the outer surface 32 toward the radially outer surface 58 of the projection 40 when the distal end portion 16 is in the non-inflated position.

The side wall 56 may form a flap, hood or lip 59 (FIGS. 6-7) when the distal end portion 16 is in the expanded position. The lip 59 helps collect a sample for the collection site. The lip 59 extends from the outer surface 58 of the projection 40 toward the proximal end portion 14. The projection 40 elongates from the shape shown in FIG. 4 to the shape shown in FIG. 6 during expansion of the distal end portion 16. The projection 40 also reduces height from the shape shown in FIG. 5 to the shape shown in FIG. 7 during expansion of the distal end portion 16. The elongation and reduction in height of the projection 40 causes the collection lip 59 to form on the collection side of the projection 40. The difference in the tapers between the side walls 54, 56 creates a bias lean of the wall section to roll toward the side wall 56. The projection 40 is biased and concave on the side wall 56 in the non-inflated state and this is further enhanced during inflation. When the elongation of the projection 40 occurs, the projection thins out and becomes less stable to remain in a vertical column which causes the top edge to roll over towards the side wall 56 which forms the lip 59 over the proximal or collection side of the projection. The side walls 54, 56 may both taper at any desired angles. It is also contemplated that the side walls 54 and 56 may not taper toward each other.

The distal end portion 16 may include a plurality of projections or bristles 60 (FIG. 1) extending from a distal portion of the distal end portion 16. The projections 60 have the same general V-shape as the projections 40 and are smaller than the projections 40. The projections 60 have first and second sides 62 and 64 that have a length smaller than the first and second sides 42, 44 of the projections 40.

The projections or bristles 40, 60 are arranged in circumferentially extending rows (FIG. 1). It is contemplated that each row has six projections 40 or 60. It is contemplated that each of the rows may have any desired number of projections 40 or 60. Each of the projections 40, 60 is circumferentially offset from the projections on an adjacent row. Ribs 66 extend circumferentially between adjacent projections 40, 60 in each row. The ribs 66 extend between ends of the side walls 54, 56 opposite the intersections 48.

The catheter 20 may have a stylet 100 (FIG. 8) that provides stiffness to the catheter 20 so that a physician or operator may place the collection portion 12 into the back of a throat of a subject for easier swallowing. The stylet 100 may extend through the catheter 20 from adjacent the first or proximal axial end portion 14 of the collection portion 12 to a connector 102. The connector 102 is connected with the catheter 20 and permits the introduction of fluid into the catheter for expanding the distal end portion 16 of the collection portion 12. The stylet 100 is preferably made of a polyether ether ketone (PEEK) polymer. However, the stylet may be a stainless-steel guidewire, a polymer monofilament extrusion and/or a stainless-steel monofilament core wire. The stylet 100 may have a rounded flexible distal end 104 (see FIG. 3) spaced from the collection portion 12. The flexible distal end 104 may be a graduated ground tip for increased flexibility. The distal end 104 may be the most flexible portion of the stylet 100.

A proximal end 106 (FIGS. 8-9) of the catheter 20 is connected to the connector 102. The connector 102 may be a Y-fitting with a first branch 110 connected to the proximal end 106 of the stylet 100. The proximal end 106 of the stylet 100 extends through the first branch 110 into a cap 112 that seals and closes the first branch. The proximal end 106 is connected to the cap 112 and the first branch 110 with epoxy and cut off flush with the proximal end of cap 112. The epoxy may connect the cap 112 to the first branch 110. It is contemplated that the stylet 100 may be fixedly connected to the cap 112, such as by insert molding. The stylet 100 may then be inserted into the Y-fitting 102 and catheter 20 and connected to the Y-fitting by the cap. The stylet 100 could then be removed from the catheter 20 and Y-fitting 102 if desired. The catheter 20 may be lubricated to permit removal of the stylet 100 from the catheter. It is also contemplated that the proximal end 106 may extend through a Tuohy-Borst adapter connected to the first branch 110 to allow a user to loosen the Tuohy-Borst adapter and remove the stylet 100 to reduce the stiffness of the catheter 20. It is also contemplated that the stylet may extend along the outside of the catheter 20.

The Y-fitting 102 has a second branch 120 extending at an angle to the first branch 110. The second branch 120 may have a stopcock 122 for opening and closing the second branch. A syringe may be connected to the second branch 120 for introducing a fluid, such as air, into the Y-fitting 102 and catheter 20 to expand the distal end portion 16 of the collection portion 12 and apply a vacuum to remove the fluid to collapse the distal end portion 16 after collecting a sample. The stopcock 122 may be used to retain the fluid in the catheter 20 and collection portion 12 when obtaining a sample. The stopcock 122 and syringe help to control the injection of fluid to move the distal end portion 16 between the collapsed and expanded positions.

A disk 126 may be connected to a proximal end of the catheter 20 or the distal end of the connector 102. The disk 126 extends radially away from the catheter 20 to prevent the connector 102 from being inserted into a subject's mouth and/or throat.

The collection portion 12 is moved to a collection site within a body lumen, such as an esophagus, with the distal end portion 16 in the collapsed or deflated position. The collection portion 12 may be swallowed by a subject. The stylet 100 may be manipulated to place the collection portion 12 into the back of the throat of the subject to help with the swallowing of the collection portion. It is also contemplated that the subject may be intubated with the collection portion 12 attached to the catheter. The distal end portion 16 may be held in the collapsed or deflated position by applying a vacuum to the collection portion 12 through the support 20. The support member 20 or catheter may have depth markings to determine the collection site within the subject's anatomy. The collection portion 12 may be moved past a lower esophageal sphincter (LES) and pulled in a proximal direction toward the LES. The operator or physician may sense the increased tension in the catheter 20 when the collection portion 12 engages the LES. The distal end portion 16 of the collection portion 12 may be expanded when the LES is sensed. The distal end portion 16 is moved from the collapsed position to the expanded position when the collection portion 12 is at or near the collection site. The syringe connected to the Y-fitting 102 may be activated to apply pressurized fluid, such as air, to the distal end portion 16 to cause the distal end portion to move axially from the collapsed position to the expanded position.

The collection portion 12 is moved in the esophagus or body lumen to collect a biological sample, such as, tissue, cells, protein, RNA and/or DNA from the collection site when the distal end portion 16 is in the expanded position. It is contemplated that the collection portion 12 is only moved in a proximal direction so that the expanded distal end portion 16 engages the collection site to collect biological samples. The depth markings on the support member 20 or catheter may be used as a guide. For example, the catheter can have markings on its length starting at 20 cm proximal to the balloon and extending to 60 cm in 5 cm increments. After the biological sample is collected, the distal end portion 16 is moved from the expanded position to the collapsed or retracted position. The distal end portion 16 may be moved from the expanded position to the collapsed position by applying a vacuum to the collection portion 12 with the syringe connected to the Y-fitting 102. As the collection portion 12 moves out of the body lumen, the distal end portion 16 does not engage the body lumen and prevents the collected biological samples from being contaminated by tissue from areas along the body lumen different from the collection site. Once the collection device 10 is removed from the subject, the biological samples are collected via a wash and/or the collection portion 12 or the distal end portion 16 may be cut from the support member 20 and deposited in a biological sample vial.

Figure 9:
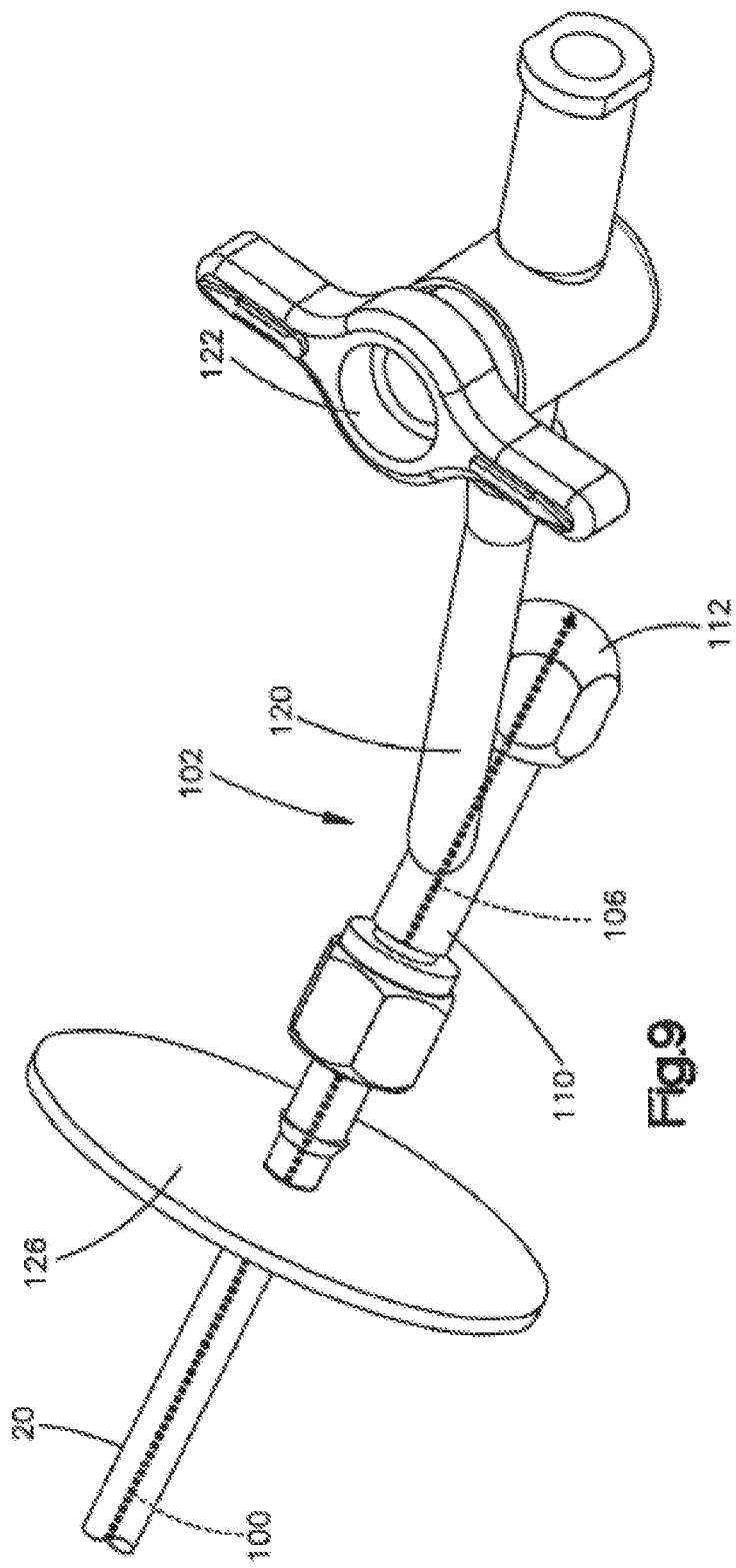
FIG. 9 is an enlarge schematic pictorial view of the connector of FIG. 8.
Figure 10:
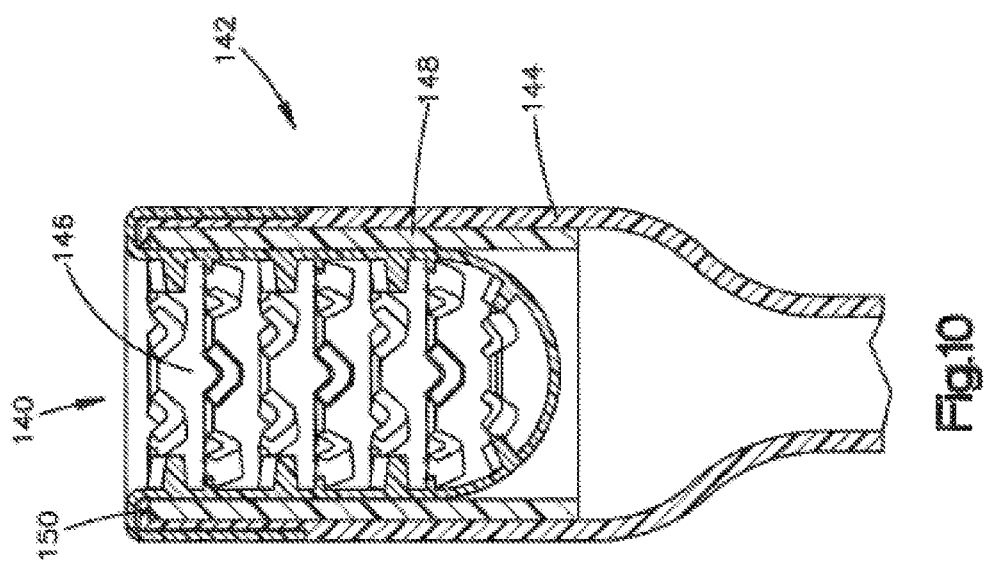
FIG. 10 is a schematic sectional view of a collection device constructed in accordance with another embodiment of the present disclosure.

Another embodiment of a collection device 140 is shown in FIG. 10. The collection device 140 is generally similar to the collection device shown in FIGS. 1-9 and has a collection portion 142 with a first or proximal end portion 144 and a second or distal end portion 146. The distal axial end portion 146 may expand and contract. The first or proximal axial end portion 144 is relatively rigid. Therefore, the proximal end portion 144 has a fixed radial extent. The second or distal end portion 146 of the collection portion 142 has an expanded or inflated position, similar to the expanded position shown in FIG. 1, and a collapsed or deflated position shown in FIG. 10. The distal end portion 146 has a convex shape when in the expanded or inflated position. The distal end portion 146 extends into the first or proximal axial end portion 144 and has a concave shape when in the collapsed or deflated position. The distal end portion 146 may be retracted when in the collapsed position. The distal end portion 146 extends axially into the interior of the proximal end portion 144 when in the collapsed or deflated position. Therefore, the distal end portion 146 moves axially or longitudinally relative to the proximal end portion 144 when moving between the deflated and inflated positions.

stiffening sleeve 148 is connected to the proximal end portion 144. The sleeve 148 may be axially inserted into the proximal end portion 144 of the collection portion 142 so that the distal end portion 146 extends into the sleeve when the distal end portion is in the collapsed position. The sleeve 148 is retained in the proximal end portion 144 by a distal undercut rim 150 on the proximal end portion. The sleeve 148 may be inserted axially into the proximal end portion 144 until the undercut rim 150 snaps over the sleeve to retain the sleeve in the proximal end portion. The undercut rim prevents the sleeve 148 form being able to slide out into the distal end portion 146. The sleeve 148 may be a polypropylene molded cylinder that provides additional column strength to the proximal end portion 144 to help prevent column and side wall collapse during vacuum retraction of the distal end portion 146. The sleeve 148 allows for a thinner wall of the proximal end portion 144. The thinner wall of the proximal end portion 144 provides more space on the inside of the proximal end portion for the distal end portion 146 to retract easier. The ease at which the distal end portion 146 retracts may enhance the ability to collect as much of the biological sample as possible. If there is too much friction between the surfaces of the distal end portion 146 as the distal end portion retracts into the proximal end portion 144 it could squeegee off the sample. The sleeve 148 enhances retraction reliability and reduces the surfaces of the distal end portion 146 from rubbing against each other during the retraction. The sleeve 148 may be a polymer and/or metallic thin wall sleeve inserted or insert molded into the proximal end portion 144. The sleeve 148 provides hoop strength and helps prevent the proximal end portion 144 from collapsing under vacuum.

The distal end portion 146 has an outer surface for collecting tissue when the distal portion is in the expanded position. The outer surface faces radially outwardly when the distal end portion 146 is in the expanded position and may face radially inwardly when the distal end portion is in the collapsed or retracted position. The outer surface of the distal end portion 146 may have a plurality of projections or bristles 152 for collecting tissue. The projections 152 may have a V-shape similar to the V-shaped projections 40 illustrated in FIGS. 1-7.

Figure 11:
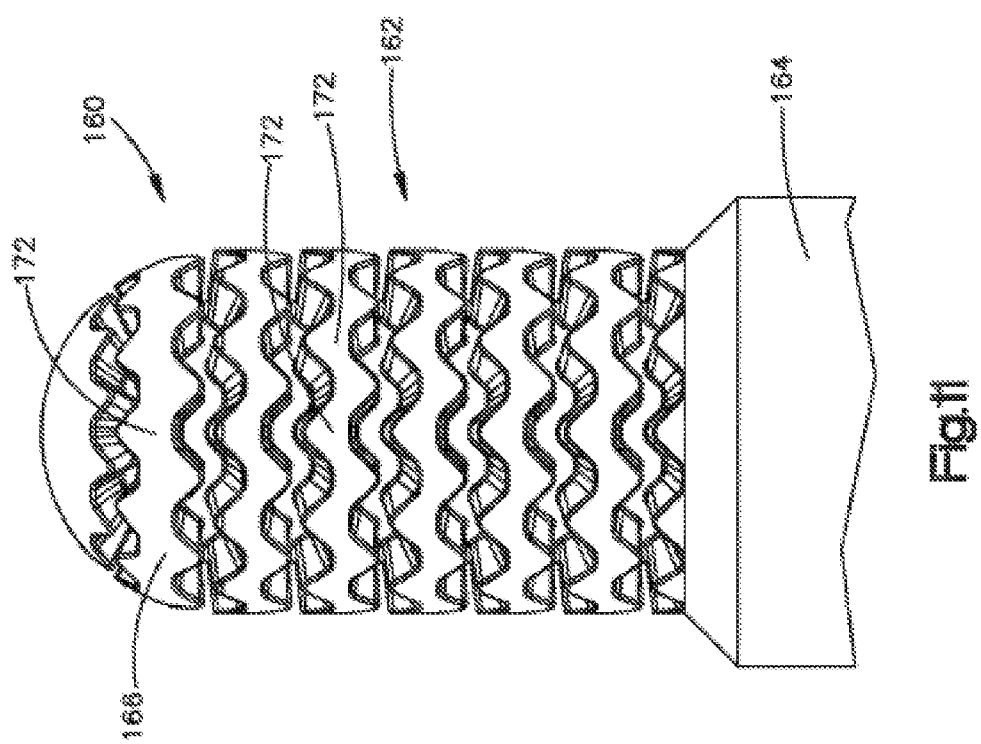
FIG. 11 is a schematic pictorial view of a collection device constructed in accordance with a third embodiment of the present disclosure.

Another embodiment of a collection device 160 is illustrated in FIG. 11. The collection device 160 is generally similar to the collection device shown in FIGS. 1-9, however, the collection device 160 illustrated in FIG. 11 has a double V texture. The collection device 160 has a collection portion 162 with a first or proximal end portion 164 and a second or distal end portion 166. The distal axial end portion 166 may expand and contract. The first or proximal axial end portion 164 is relatively rigid. Therefore, the proximal end portion 164 has a fixed radial extent. The second or distal end portion 166 of the collection portion 162 has an expanded or inflated position, similar to the expanded position shown in FIG. 1, and a collapsed or deflated position, similar to the collapsed position shown in FIG. 3. The collection portion 162 is shown in FIG. 11 in a non-inflated position between the expanded and collapsed positions. The distal end portion 166 has a convex shape when in the expanded or inflated position. The distal end portion 166 extends into the first or proximal axial end portion 164 and has a concave shape when in the collapsed or deflated position. The distal end portion 166 extends axially into the interior of the proximal end portion 164 when in the collapsed or deflated position. Therefore, the distal end portion 166 moves axially or longitudinally relative to the proximal end portion 164 when moving between the deflated and inflated positions.

The distal end portion 166 has an outer surface for collecting tissue when the distal portion is in the expanded position. The outer surface faces radially outwardly when the distal end portion 166 is in the expanded position and may face radially inwardly when the distal end portion is in the collapsed or retracted position. The outer surface of the distal end portion 166 may have a plurality of projections or bristles 172 for collecting tissue. The projections 172 may form a double V-shape. Each of the projections 172 is similar to the V-shaped projections 40 illustrated in FIGS. 1-7. Each V-shaped projection 172 is connected directly to an adjacent V-shaped projection.

Another embodiment of a collection device 180 is illustrated in FIG. 12. The collection device 180 is generally similar to the collection device shown in FIGS. 1-9 and has a collection portion 182 with a first or proximal end portion 184 and a second or distal end portion 186. The distal axial end portion 186 may expand and contract. The first or proximal axial end portion 184 is relatively rigid. Therefore, the proximal end portion 184 has a fixed radial extent. The second or distal end portion 186 of the collection portion 182 has an expanded or inflated position, similar to the expanded position shown in FIG. 1, and a collapsed or deflated position shown in FIG. 12. The distal end portion 186 has a convex shape when in the expanded or inflated position. The distal end portion 186 extends into the first or proximal axial end portion 184 and has a concave shape when in the collapsed or deflated position. The distal end portion 186 may be retracted when in the collapsed position. The distal end portion 186 extends axially into the interior of the proximal end portion 184 when in the collapsed or deflated position. Therefore, the distal end portion 186 moves axially or longitudinally relative to the proximal end portion 184 when moving between the deflated and inflated position.

The distal end portion 186 has an outer surface for collecting tissue when the distal portion is in the expanded position. The outer surface faces radially outwardly when the distal end portion 186 is in the expanded position and may face radially inwardly when the distal end portion is in the collapsed or retracted position. The outer surface of the distal end portion 186 may have a plurality of projections or bristles 192 for collecting tissue. The projections 192 may have a V-shape similar to the V-shaped projections 40 illustrated in FIGS. 1-7.

The collection device 180 includes a gel cap or gelatin cover or cap 194 that may be loaded over an end of the collection portion 182. The cap 194 holds the distal end portion 186 in the collapsed position during insertion and movement of the collection portion 182 to the collection site. The cap 194 falls off, pops off and/or dissolves when the collection portion 182 reaches the body lumen. The cap 194 may fall off in response to the movement of the distal end portion 186 from the collapsed position to the expanded position.

Another embodiment of a collection device 200 is illustrated in FIG. 13. The collection device 200 is generally similar to the collection device shown in FIGS. 1-9 and has a collection portion 202 with a first or proximal end portion 204 and a second or distal end portion 206. The distal axial end portion 206 may expand and contract. The first or proximal axial end portion 204 is relatively rigid. The second or distal end portion 206 of the collection portion 202 has an expanded or inflated position, similar to the expanded position shown in FIG. 1, and a collapsed or deflated position shown in FIG. 13. The distal end portion 206 has a convex shape when in the expanded or inflated position. The distal end portion 206 extends into the first or proximal axial end portion 204 and has a concave shape when in the collapsed or deflated position. The distal end portion 206 may be retracted when in the collapsed position. The distal end portion 206 extends axially into the interior of the proximal end portion 204 when in the collapsed or deflated position. Therefore, the distal end portion 206 moves axially or longitudinally relative to the proximal end portion 204 when moving between the deflated and inflated position.

The distal end portion 206 has an outer surface for collecting tissue when the distal portion is in the expanded position. The outer surface faces radially outwardly when the distal end portion 206 is in the expanded position and may face radially inwardly when the distal end portion is in the collapsed or retracted position. The outer surface of the distal end portion 206 may have a plurality of projections or bristles 212 for collecting tissue. The projections 212 may have a V-shape similar to the V-shaped projections 40 illustrated in FIGS. 1-7.

The collection device 200 includes a weight 214 connected to the proximal end portion 204. The weight 214 may aid in swallowing the collection portion 202. The weight 214 may be made of tungsten and inserted into the proximal end portion 204. It is contemplated that the weight 214 may be insert molded to the proximal end portion 204.

Figure 8:
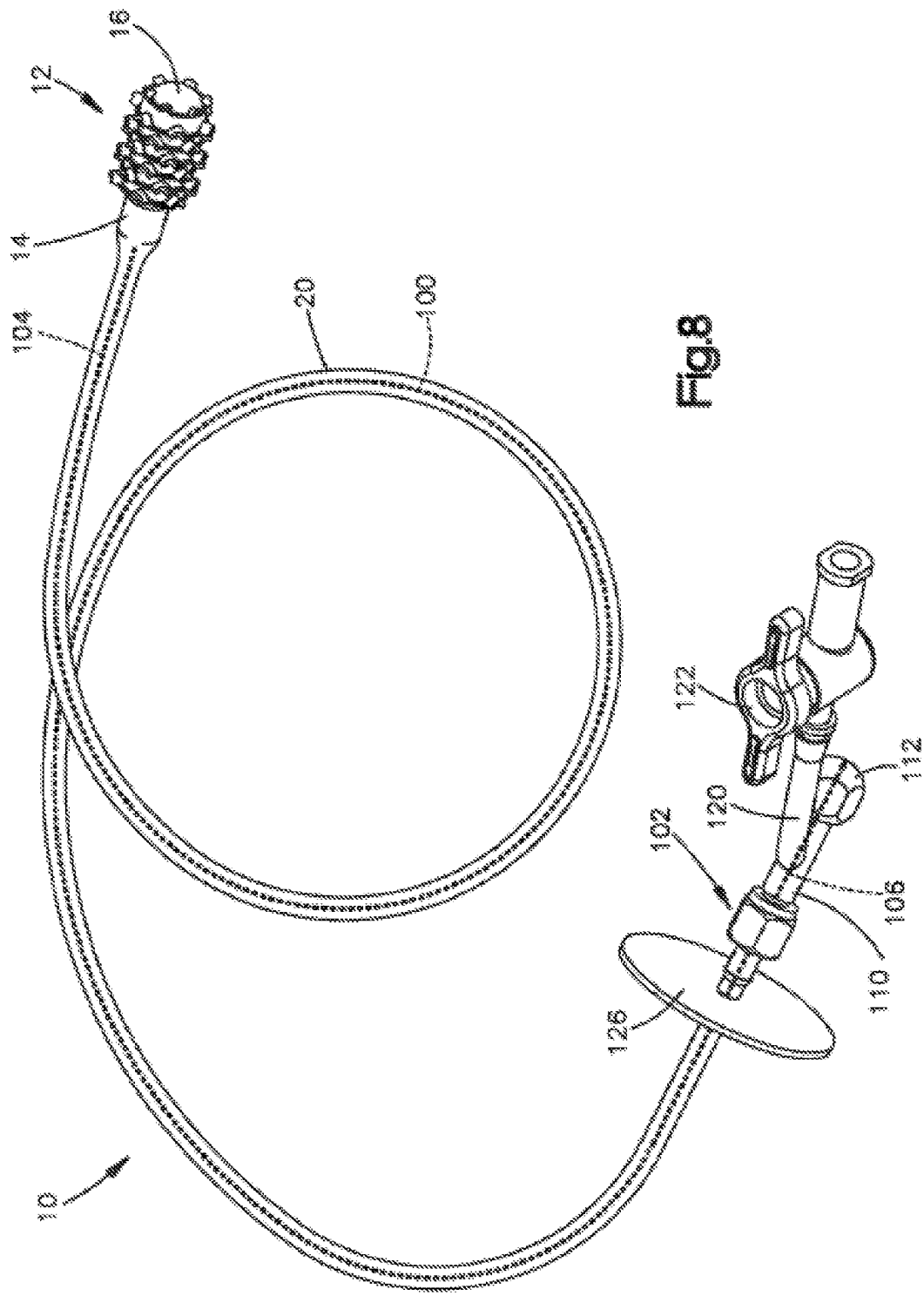
FIG. 8 is a schematic pictorial view of the collection device showing a stylet and connector of the collection device.

The collection devices 140, 160, 180 and 200 may be used with the catheter 20, stylet 100, and/or connector 102 of FIGS. 8-9. It is also contemplated that the sleeve 148, cap 194 and/or the weight 214 may be used together or separately with any of the collection devices In some embodiments, a device 300 for collecting a biological sample in a subject. The device 300 can include an inflatable distal end portion 316 attached to a tubular support member 20. The inflatable distal end portion 316 can be designed to expand from within a proximal end portion 314 that is coupled to or part of the tubular support member 20. The inflatable distal end portion 316 can be inflated to be extended outward from the proximal end portion 314 and deflated to retract within the proximal end portion 314. In some embodiments, a surface on the inflatable distal end portion 316 can be provided with varied thickness to facilitate movement of the inflatable distal end portion 316 between an expanded state and a deflated and retracted state. The varied thickness of the inflatable distal end portion 316 can be provided to assist in any combination of inflation, expansion, deflation, and retraction of the inflatable distal end portion 316 in relation to the proximal end portion 314. The varied thickness can also influence the shape and flexibility/rigidity of the inflatable distal end portion 316 when in any of the any combination of inflation, expansion, deflation, and retraction states. In some embodiments, the surface of the inflatable distal end portion 316 can include a plurality of projections or bristles 312 positioned on the surface to allow collection of a biological sample when the inflatable distal end portion 316 is in the expanded state. The projections or bristles 321 positioned on the surface of the inflatable distal end portion 316 can also be accompanied by formations (e.g., ridges, valleys, etc.) formed by the varied thickness of the inflatable distal end portion. The formations created by the varied thickness of the surface can also assist in cell collection as well as the transition between states of the inflatable distal end portion 316.

Figure 14:
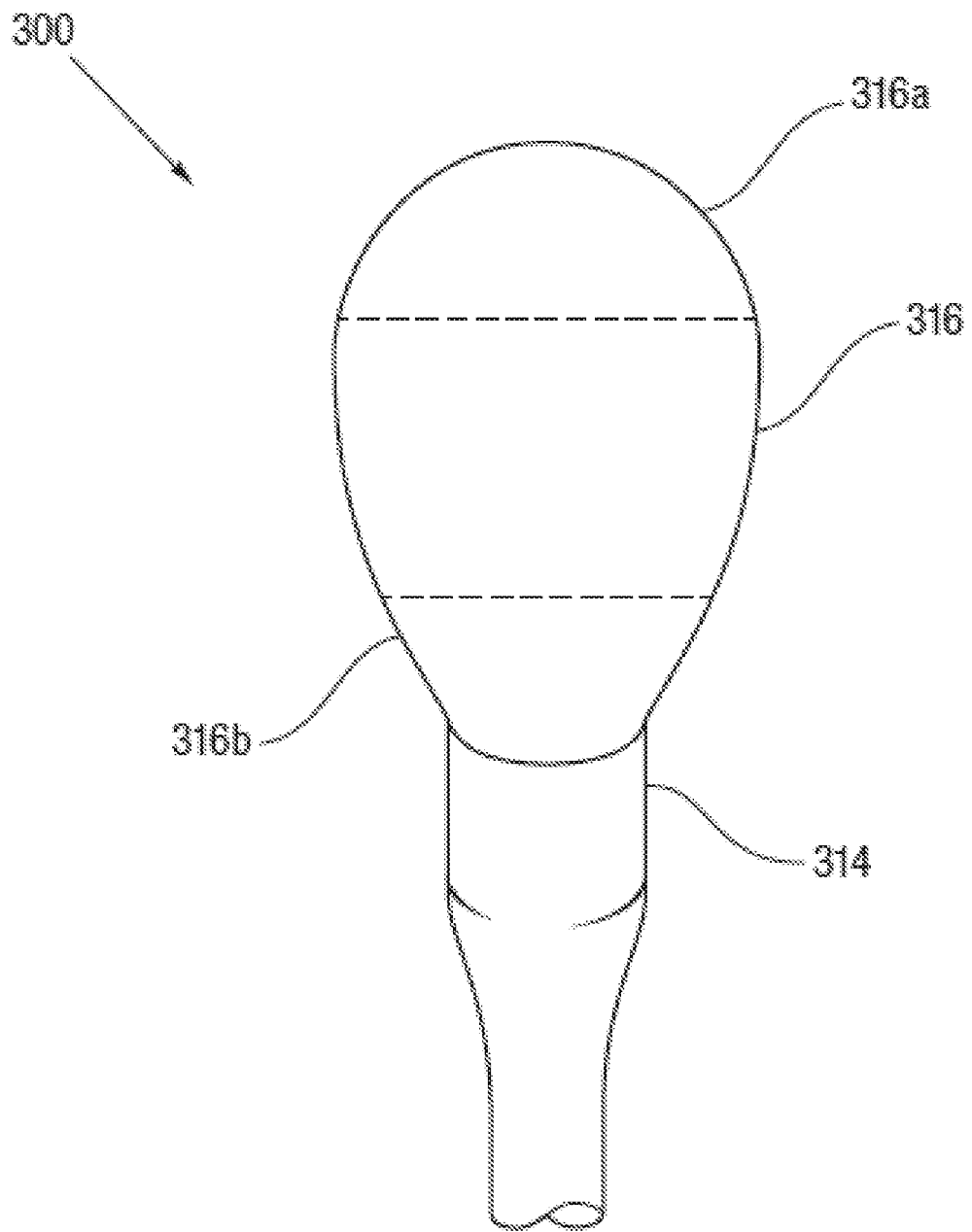
FIG. 14 is a schematic sectional view of a collection device constructed in accordance with an example embodiment of the present disclosure.

Referring to FIG. 14, in some embodiments, a collection device 310 can be designed for structured retraction of a distal end portion 316 into a proximal end portion 314, similarly as discussed with respect to collection devices 140, 160, 180 and 200. FIG. 14 shows an example illustration of the distal end portion 316 inflated and expanded from the proximal end portion 314 and at least partially inflated. To facilitate more predictable and consistent deflation and retraction of the distal end portion 316 into the proximal end portion 314, the structure of the distal end portion 316 can be sized, shaped, constructed from a combination of materials, constructed using a combination of durometer, or a combination thereof that enable predictable deflation and retraction of the distal end portion 316. In some embodiments, the distal end 316a of the distal end portion 316 can be constructed to be thinner in thickness and/or formed from a material that is thinner than that of the proximal end 316b of the distal end portion 316. The thinner distal end 316a of distal end portion 316 can be provided to facilitate improved deflation and retraction of the distal end portion 316.

Continuing with FIG. 14, the construction of the distal end portion 316 can have varied levels of durometer to facilitate controlled deflation and retraction into the proximal end portion 314. In some embodiments, the distal end 316a of the distal end portion 316 can be constructed from a material with a lower durometer than the material of the proximal end 316b of the distal end portion 316. The lower durometer of the distal end 316a of distal end portion 316 can be provided to facilitate improved deflation and retraction of the distal end portion 316. For example, the distal end 316a of the distal end portion 316 can be a silicone material that has a durometer between approximately 20 and 30 Shore A and the proximal end 316b can be a silicone material that has a durometer between approximately 40 and 50 Shore A.

In some embodiments, the distal end portion 316 can include any combination of different levels of durometer at different locations to improve any of inflation, expansion, biological cell collection, deflation, and retraction into the proximal end portion 314. For example, the material of the distal end portion 316 can be decreasing in durometer level from the proximal end 316b with the highest durometer level to the distal end 316a, with the distal end 316a having the lowest durometer level. In another example, the durometer level at a middle portion between the proximal end 316b to the distal end 316a can be the lowest durometer level.

Figure 15:
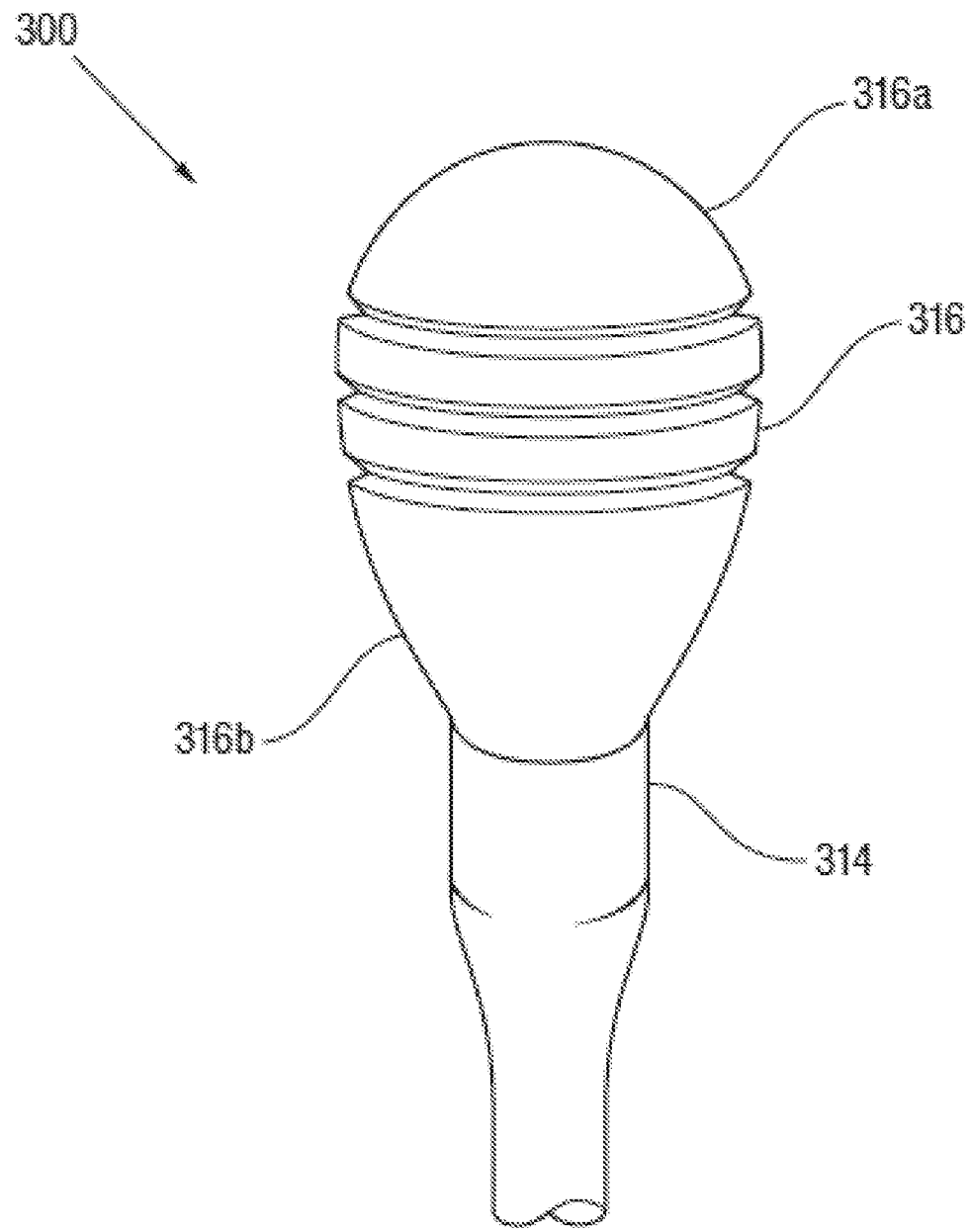
FIG. 15 is a schematic sectional view of a collection device constructed in accordance with an example embodiment of the present disclosure.

Referring to FIG. 15, in some embodiments, the distal end portion 316 can be designed to collapse in a tiered, stackable, and/or compressible structure. For example, as depicted in FIG. 15, the distal end portion 316 can have a plurality of collapsible folds forming an accordion or similar design to facilitate deflation and retraction into the proximal end portion 314. FIG. 15 shows an example illustration of the distal end portion 316 inflated and expanded from the proximal end portion 314 and at least partially inflated. In addition to the shapes, each of the collapsible sections can have different durometer levels to insure even compression. The collapsible sections can be formed using any combination of methods. For example, the distal end portion 316 can be formed entirely using a mold or formed using a combination of steps, such as using a mold then forming the folds as a secondary process using a heated die. In some embodiments, the accordion design can include a combination of different materials for the inner folds and the outer folds to maintain the shape of the distal end portion 316 as well as the inflation, expansion, deflation, and retraction of the distal end portion 316.

Figure 16:
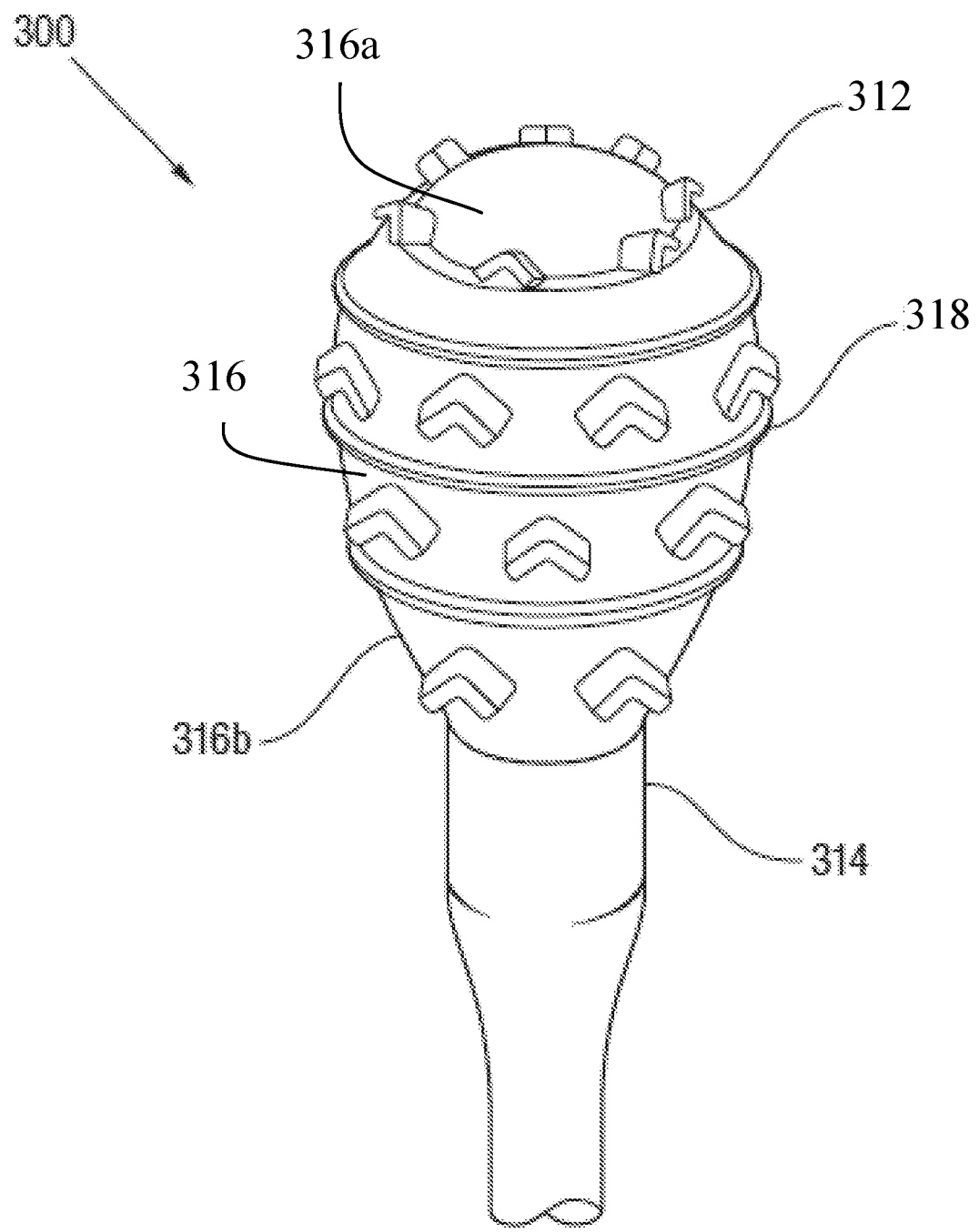
FIG. 16 is a schematic sectional view of a collection device constructed in accordance with an example embodiment of the present disclosure.
Figure 17:
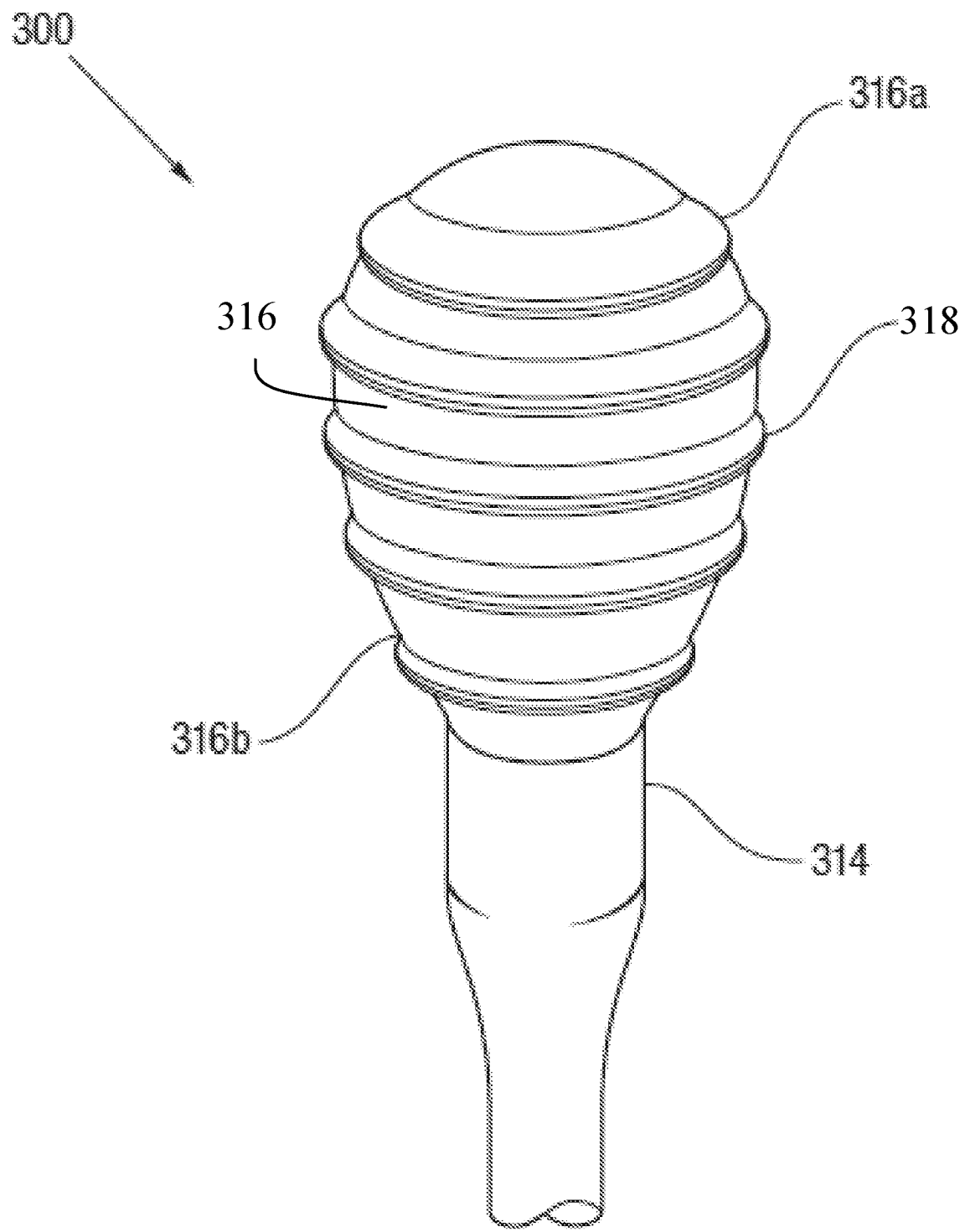
FIG. 17 is a schematic sectional view of a collection device constructed in accordance with an example embodiment of the present disclosure.

Referring to FIGS. 16 and 17, in some embodiments, the distal end portion 316 can be designed to include additional structure for providing varying stiffness of the distal end portion 316. FIGS. 16 and 17 show example illustrations of the distal end portion 316 inflated and expanded from the proximal end portion 314 and at least partially inflated. The additional structure can include projections or bristles 312 as discussed with respect to the projections or bristles 40, 60, 152, 212, as well as additional structural features. For example, as depicted in FIG. 16, the distal end portion 316 can include a plurality of ridges 318 located between the projections or bristles 312 (e.g., chevron shapes) on the surface of the distal end portion 316. The plurality of ridges 318 can be provided to vary inflation size and shape of distal end portion 316. The ridges 318 may also be designed to assist the projections or bristles 312 in the collection of biological samples. For example, the ridges 318 can be sized and shaped such that they are capable of capturing a target biological material(s).

In some embodiments, as depicted in FIG. 17, the ridges 318 can be provided as structural features as well as the primary cell collection elements of the distal end portion 316. The ridges 318 can be formed from any combination of materials, at any combination of shapes and sizes with any combination of durometer. In some embodiments, the ridges 318 can be formed from the same material as the distal end portion 316 either as part of a same molding process to make the distal end portion 316 or as a separate process formed on a surface of the distal end portion 316. In some embodiments, the ridges 318 can have a rectangular cross-section made from the same material (e.g., silicone) as the rest of the distal end portion 316. The ridges can also be other shapes such as semicircular shapes, triangular, or any polygonal shapes or a combination of different shapes.

Figure 18:
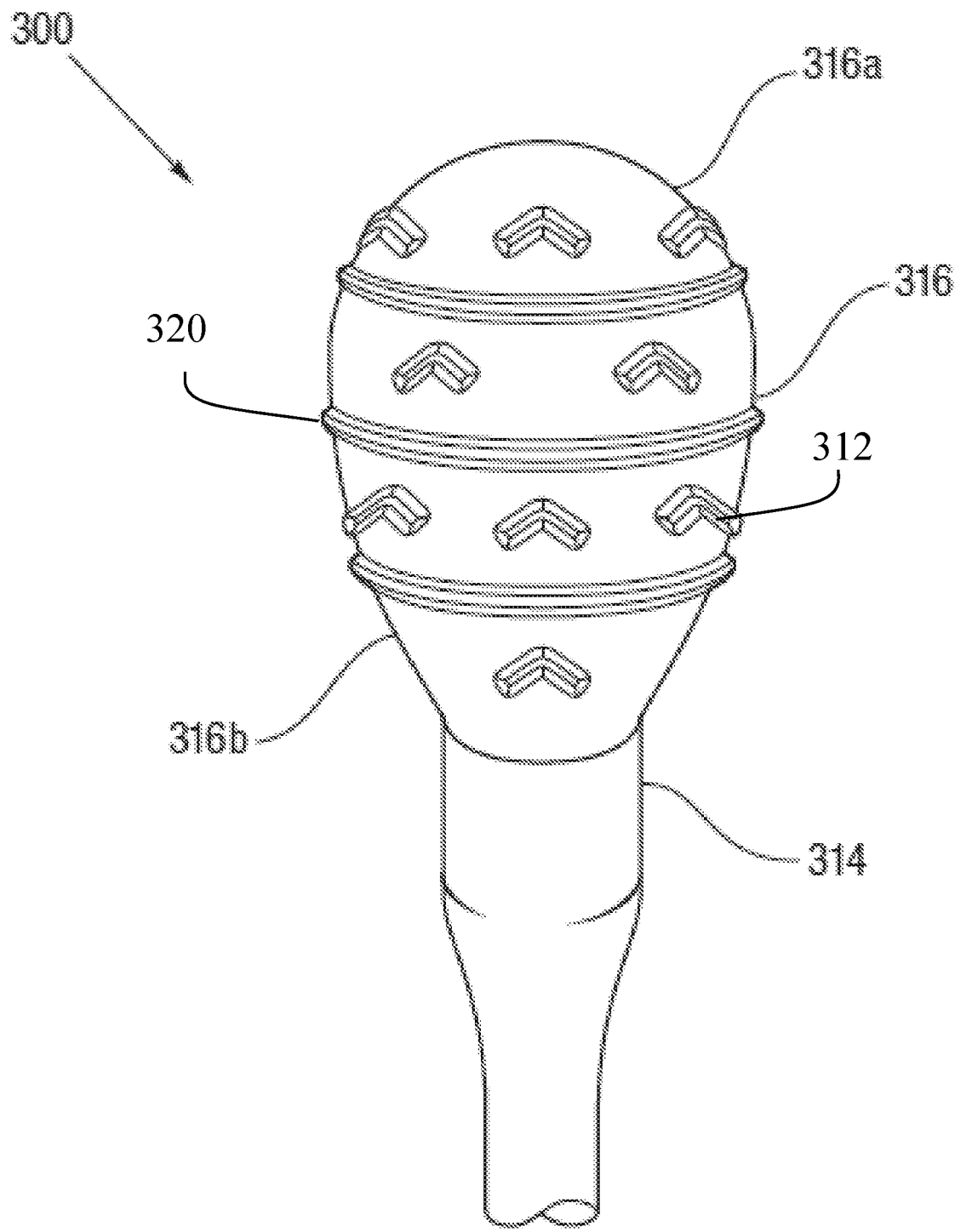
FIG. 18 is a schematic sectional view of a collection device constructed in accordance with an example embodiment of the present disclosure.

Referring to FIG. 18, in some embodiments, the distal end portion 316 can be designed to include additional structure for providing varying stiffness of the distal end portion 316. For example, the distal end portion 316 can include drafting 320 along the length of projections or bristles 312 to create a variable stiffness. The drafting 320 can be created from any combination of sizes, shapes, and/or materials, including the same material as the rest of the distal end portion 316 with a higher durometer level or a different material with a higher level of stiffness. For example, the drafting can range from a half a degree to several degrees.

FIG. 18 shows an example illustration of the distal end portion 316 inflated and expanded from the proximal end portion 314 and at least partially inflated.

As would be appreciated by one skilled in the art, the collection device 300, and particularly the distal end portion 316, can be designed for a particular inflation and expansion qualities, including any combination of the designs discussed with respect to the deflation and retraction designs discussed with respect to FIGS. 14-18.

In some embodiments, the distal end portion 316 may be connected to the proximal end portion 14 in a replaceable and removable manner. In other words, the distal end portion 316 can be removed from the proximal end portion 314 without needing to damage the distal end portion 316 (e.g., by cutting it off the proximal end portion 314). The distal end portion 316 can be removably coupled to the proximal end portion 314 using any combination of methods and systems. For example, the distal end portion 316 can be threaded onto the proximal end portion 314 and/or it can be held onto the proximal end portion 314 using a friction fit, adhesive, or through a mechanical connection. Having the distal end portion 316 being removeable enables the rest of the collection device 300, including the proximal end portion 314 to be cleaned and reused. Once removed, the distal end portion 316 can be packaged and/or sent for analysis of any collected biological samples. In some embodiments, the proximal end portion 314 can be removable from the catheter 20 and the combination of the retracted distal end portion 316 and the proximal end portion 314 can be provided for analysis. The proximal end portion 314 can be removable and replaceable from the catheter 20 using any combination of methods, such as the ones discussed here with respect to the removable and replaceable distal end portion 316.

Any combination of elements from FIGS. 1-18 can be combined to form a collection device in accordance with the present disclosure. From the above description of the invention, those skilled in the art will perceive improvements, changes and modifications. Such improvements, changes and modifications are intended to be covered by the appended claims.

In operation, the collection device 10, 160, 180, 200, 300 can be used for collecting biological samples within a target location of a subject. For example, the collection device 300 can be used for collecting any combination of tissue, cells, protein, RNA and/or DNA in an esophagus of a subject. The collection device 300 can be provided as part of a kit that can be pre-assembled or that needs to be assembled prior to the biological sample collection process. For example, the kit can include a coiled catheter 20 proximally coupled to a connector 102 and distally coupled to a removable and replaceable proximal end portion 314 and/or distal end portion 316. The kit can include any combination of components discusses herein. In some embodiments, the kit can also include one or more syringes for controlling the inflation, expansion, deflation, and/or retraction of the distal end portion 316. The components of the kit can be inspected, assembled, and prepped for use with a subject. For example, the proximal end portion 314 and/or distal end portion 316 can be dipped in clean water to simulate and provide lubricity.

In some embodiments, the one or more syringes can be preterminal sizes/volumes to accurately perform the various inflation, expansion, deflation, and/or retraction steps. For example, a 10-30 cc syringe can be used to prepare the collection device 300 by depressing the 10-30 cc syringe for connection to the stopcock 122 pulling back on the syringe to 10-15 cc of draw vacuum, which will retract the distal end portion 316 completely back inside the proximal end portion 314. Thereafter, the stopcock 212 can be closed to hold the distal end portion 316 retracted inside of the proximal end portion 314 and the syringe can be removed.

Once the collection device 300 is prepped, the subject can be prepared for swallowing the proximal end of the catheter 20, including the proximal end portion 314 and distal end portion 316. For example, the subject can be sitting up and/or a topical anesthetic spray and/or viscous lidocaine can be applied to the pharynx to minimize gag reflex. Thereafter, the proximal end portion 314 and distal end portion 316 can be passed to the back of the subject's mouth to be swallowed. As the subject swallows, it should be ensured that the length of the catheter 20 is free to follow along and does not restrict the distal end portion 316 from being swallow down into a subject's stomach. As the subject swallows the proximal end portion 314 and distal end portion 316, the subject can sip small amounts of water. Subject may also be offered an appropriate topical anesthetic spray and/or viscous lidocaine applied to the pharynx to minimize gag reflex.

Once swallowed peristalsis assists in the advancement of the catheter 20 and the proximal end portion 314 and distal end portion 316 to the desired location. In some embodiments, the catheter 20 can have markings to give an estimated location of the proximal end portion 314 and distal end portion 316. For example, the proximal end portion 314 and distal end portion 316 can be estimated to be in the stomach when the markings on the catheter shows 50 cm at the dental arches. A 2-12 cc syringe (preferably 5 cc), connected to the stopcock 212, can be used to deliver 2.6-12.6 cc of air through the catheter 20 to the proximal end portion 314 and distal end portion 316, which is the amount of air that is delivered when the plunger is pulled all the way back. Once the proximal end portion 314 and distal end portion 316 are located within the stomach, as judged by the markings or other confirmation method, 2.6-12.6 cc (preferably 5.6 cc) of fluid (e.g., air, gas, liquid, etc.) can be injected from a syringe through the catheter 20 to inflate and/or expand the distal end portion 316. In some instances, the portion of the distal end portion 316 can be confirmed using other methods, such as a stethoscope or using imaging devices. In some embodiments, when in place, the distal end portion 316 can be inflated to 16-18 mm diameter. Thereafter, the stopcock 212 can be closed and the 2-12 cc syringe can be removed.

In some embodiments, with the distal end portion 316 inflated within the stomach, the physician can gently pull back on the catheter 20 until a moderate resistance is felt as a result of the distal end portion 316 contacting the lower esophageal sphincter (LES) at the gastro-esophageal junction (GEJ). Once the LES/GEJ is contacted by the distal end portion 316, the catheter 20 markings at the dental arches can be noted. With the markings noted, the physician can continue to pull the distal end portion 316 from the location proximal to the LES/GEJ for about 2 to 15 cm to gather a sample (e.g., abnormal columnar epithelial cells that could indicate Barrett's Esophagus (BE)) from the distal portion of the esophagus. As the distal end portion 316 passes through the LES/GEJ there may be a greater level of resistant until the LES relaxes and the distal end portion 316 moves more freely. Once the distal end portion 316 passes through the LES/GEJ, the stretch of the catheter 20 can subside and then provide a more accurate measure for the sampling length of approximately 2 to 15 cm.

In some embodiments, a subject may have a patulous GEJ which can be identified if a user does not feel the LES/GEJ despite the balloon being pulled all the way back to above 30 cm from the dental arches. In such instances, additional steps can be taken to assist in identifying the location of the LES before sampling. Initially, the stopcock 212 can be opened and draw a vacuum (e.g., using a 5-20 cc syringe) and invert the distal end portion 316 into the proximal end portion 314. Thereafter, the stopcock 212 can be moved into a closed position and the proximal end portion 314 can be re-advanced into the subject's stomach until the markings on the catheter 20 shows 50 cm on at the dental arches. Once in place, the stopcock 212 can be opened and 11 cc (e.g., of air) can be inserted into the catheter 20 to inflate the distal end portion 316 and the stopcock 212 can be closed to hold the inflation within the distal end portion 316. Thereafter, the catheter 20 can be gently pulled back until moderate resistance is felt, signifying that the distal end portion 316 is contacting the LES. This location can be noted based on the markings near the dental arches to indicate the location of the LES. With the location known, the distal end portion 316 can be withdrawn into the proximal end portion 314 (e.g., by applying a vacuum) and the normal steps can be performed with the known location of the LES. For example, using a balloon inflation of about. 2.6-12.6 cc (preferably 5.6 cc) and using the location of the LES in cm from the dental arches.

In some embodiments, once the distal end portion 316 has been moved the desired distance within the esophagus, it can be deflated and retracted within the proximal end portion 314 to protect any collected biological sample during withdrawal of the device 200. For example, once the distal end portion 316 is pulled across the sample location at the distal esophagus, the stopcock 212 can be opened to deflate the distal end portion 316. Once deflated, another syringe, for example a 15-25 cc syringe can be connected to the stopcock 212 to withdraw 5-20 cc of fluid from the catheter 20 to retract the distal end portion 316 with the distal esophageal sample protected within the proximal end portion 314. The stopcock 212 can then be closed and the 15-25 cc syringe removed.

With the sampling distal end portion 316 protected within the proximal end portion 314, the catheter 20 can be removed. The catheter 20 can be removed, including the proximal end portion 314 and distal end portion 316, entirely from the esophagus/mouth by pulling back on the catheter 20. The proximal end portion 314 and distal end portion 316 may feel like it is stuck at the upper esophageal sphincter momentarily and will require a firm tug to extract the collection device 300 in its entirety. In some embodiments, the physician may ask the subject to swallow while pulling the proximal end portion 314 and distal end portion 316 across the upper esophageal sphincter for easier removal. This will relax the upper sphincter and make it easier to extract the proximal end portion 314 and distal end portion 316.

In some embodiments, once removed, the proximal end portion 314 and distal end portion 316 can be preserved from contamination, for example, placing the proximal end portion 314 and/or distal end portion 316 within a sealable container (e.g., a vial, sample bag, etc.). In some embodiments, the distal end portion 316 is removed from the proximal end portion 314. For example, a 2-12 cc syringe can be used to deliver 1-5 cc of fluid to inflate the distal end portion 316. The fluid should be delivered at a slow rate to ensure that the biological sample is not inadvertently pushed off of the distal end portion 316. Thereafter, the syringe should be removed and the stopcock 212 remain open to deflate the distal end portion 316. Without touching the surface of the distal end portion 316 and the collected sample, the distal end portion 316 can be removed. For example, the distal end portion 316 can be cut off the proximal end portion 314, it can be decoupled (e.g., mechanical connection), unscrewed, removed from the friction fit, etc. The removed distal end portion 316 can be inserted into any type of container for storage, shipping, and/or future analysis. In some embodiments, in removable and replaceable distal end portion 316 embodiments, the collection device 300 can be sanitized for future use and to receive a new distal end portion 316.

As would be appreciated by one skilled in the art, the quantities and means provided in herein are from exemplary purposes only. For example, although the use of different size syringes are provided, any combination of mechanisms for adding or removing pressure from the catheter 20 and distal end portion 316 can be used without departing from the scope of the present invention. Similarly, the ranges or markings can vary based on subject, application, etc. without departing from the scope of the present invention.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A device for collecting a biological sample in a subject, the device comprising:
   a tubular member along which fluid can be directed;
   a collection mechanism having (a) a proximal portion attached to a distal end of the tubular member, (b) a distal inflatable portion designed (i) to extend distally from within the proximal portion and expand when inflated and (ii) to retract within the proximal portion, (c) a wall of the distal inflatable portion provided with different durometer levels along its length such that the distal inflatable portion has a lower durometer than the proximal portion and (d) a plurality of circumferential geometric features radially extending from an outer surface of the collection mechanism, the plurality of circumferential geometric features defining varied thickness of the collection mechanism, to facilitate a combination of inflation, expansion, deflation, and retraction of the distal inflatable portion, in connection with movement of the distal inflatable portion between an expanded state and a retracted state;
   a plurality of projections on a surface of the wall to allow collection of the biological sample when the distal inflatable portion is in the expanded state; and
   a weight connected to the proximal portion to facilitate swallowing the collection mechanism.

2. A device of claim 1, wherein the varied thickness is defined by collapsible folds circumferentially situated about the surface of the inflatable portion.

3. A device of claim 1, wherein the collection mechanism is removable from and replaceable on the tubular member using at least one of a friction fit or a mechanical fit.

4. A device of claim 1, wherein the varied thickness is defined by a plurality of ridges circumferentially positioned about the surface of the inflatable portion.

5. The device of claim 4, wherein the plurality of ridges are positioned between each row of the plurality of projections to vary inflation size and shape of the inflatable portion.

6. The device of claim 4, wherein the plurality of ridges help collect the biological sample.

7. The device of claim 4, wherein the inflatable portion includes drafting extending along a length of each row of the plurality of projections to create a variable stiffness of the inflatable portion.

8. The device of claim 1, wherein the tubular member is a catheter coupled to the collection mechanism at a distal end and a connector at a proximal end.

9. The device of claim 8, wherein the connector is a Y-fitting with a first branch extending at an angle to a second branch of the connector, the second branch including a stopcock.

10. The device of claim 1, wherein the inflatable portion has an outer surface facing radially outwardly when the inflatable portion is in an expanded condition, the outer surface facing radially inwardly when the inflatable portion is in an retracted position.

11. The device of claim 4, wherein a first side wall of a tissue collecting projection extends generally perpendicular to the surface of the inflatable portion and a second side wall of the tissue collecting projection tapers toward the first side wall as the side walls extend radially outward from the surface when the inflatable portion is in a non-inflated position between retracted and expanded positions.

12. The device of claim 11, wherein at least one of the plurality of projections has a V-shape, the first side wall facing in a proximal direction and forming an inner wall of the V-shape, the second side wall facing in a distal direction and forming an outer wall of the V-shape.

13. The device of claim 1, wherein the inflatable portion has a durometer between 20-70 Shore A.

14. The device of claim 1, further including a cap extending over the inflatable portion when the inflatable portion is in a retracted position to retain the inflatable portion in the retracted position.

15. The device of claim 1, wherein the expanded state is facilitated by presence of positive pressure.

16. The device of claim 1, wherein the retracted state is facilitated by presence of negative pressure.

* * * * *